US012409083B2

(12) United States Patent
Solomon

(10) Patent No.: US 12,409,083 B2
(45) Date of Patent: Sep. 9, 2025

(54) PATIENT INCONTINENCE PAD WITH INTEGRATED SUPPORT AND LIFTING MEMBER

(71) Applicant: Arise Healthcare Products, Inc., Oakdale, CA (US)

(72) Inventor: Charleen Suzanne Solomon, Oakdale, CA (US)

(73) Assignee: Arise Healthcare Products, Inc., Oakdale, CA (US)

( * ) Notice: Subject to any disclaimer, the term of this patent is extended or adjusted under 35 U.S.C. 154(b) by 377 days.

(21) Appl. No.: 17/705,986

(22) Filed: Mar. 28, 2022

(65) Prior Publication Data

US 2022/0362074 A1    Nov. 17, 2022

Related U.S. Application Data

(60) Provisional application No. 63/188,038, filed on May 13, 2021.

(51) Int. Cl.
*A61F 13/62* (2006.01)
*A61F 5/48* (2006.01)
(Continued)

(52) U.S. Cl.
CPC ............ *A61F 13/622* (2013.01); *A61F 5/485* (2013.01); *A61F 13/47* (2013.01); *A61F 13/505* (2013.01); *A61G 7/001* (2013.01); *A61F 2013/15146* (2013.01); *A61F 2013/15154* (2013.01); *A61F 2013/5661* (2013.01)

(58) Field of Classification Search
CPC .......... A61F 5/48; A61F 5/485; A61F 13/622; A61F 13/47; A61F 13/505; A61F 2013/15146; A61F 2013/15154; A61F 2013/5661; A61F 2013/15056;
(Continued)

(56) References Cited

U.S. PATENT DOCUMENTS 3,576,039 A * 4/1971 Roberts .................. A61F 5/485
                                              5/500
4,536,903 A * 8/1985 Parker .................... A61G 7/001
                                              5/632
(Continued)

FOREIGN PATENT DOCUMENTS

WO    2016135714 A2    9/2016

OTHER PUBLICATIONS

International Preliminary Report on Patentability issued by WIPO in connection with PCT/US2022/027826 dated Nov. 23, 2023.
(Continued)

*Primary Examiner* — Catharine L Anderson
*Assistant Examiner* — Arjuna P Chatrathi
(74) *Attorney, Agent, or Firm* — Levenfeld Pearlstein, LLC

(57) ABSTRACT

An easily changed incontinence pad has an integrated support and lifting member. The pad has a main body having an upper portion and a lower portion, and an incontinence member positioned on the lower portion. The support and lifting member forms the upper portion, and is integrated with and separable from the lower portion. The main body is a generally T-shaped body, and the support and lifting member forms first and second arms of the T-shaped body. A method of changing an incontinence pad is also disclosed.

13 Claims, 5 Drawing Sheets

(51) Int. Cl.
  *A61F 13/15*    (2006.01)
  *A61F 13/47*    (2006.01)
  *A61F 13/505*   (2006.01)
  *A61F 13/56*    (2006.01)
  *A61G 7/00*     (2006.01)

(58) Field of Classification Search
  CPC .. A61F 2013/15073; A61F 2013/49066; A61F 2013/49077; A61G 7/001; A01K 1/0157
  See application file for complete search history.

(56) References Cited

U.S. PATENT DOCUMENTS

| | | | |
|---|---|---|---|
| 6,073,279 A | 6/2000 | Skaler | |
| 6,651,278 B2* | 11/2003 | Ghanem | A47G 9/02 5/923 |
| 8,082,612 B2* | 12/2011 | Saunders | A47C 27/007 5/502 |
| 8,161,583 B1* | 4/2012 | Palen | A61G 7/1026 5/81.1 HS |
| 9,066,842 B2* | 6/2015 | Partridge | A61G 7/001 |
| 2009/0183309 A1* | 7/2009 | Stinson | A61G 7/001 5/81.1 T |
| 2016/0242966 A1* | 8/2016 | Solomon | A61F 13/64 |

OTHER PUBLICATIONS

International Search Report issued by ISA/EPO in connection with PCT/US2022/027826 issued on Jul. 25, 2022.
Written Opinion issued by ISA/EPO in connection with PCT/US2022/027826 issued on Jul. 25, 2022.

\* cited by examiner

PATIENT INCONTINENCE PAD WITH INTEGRATED SUPPORT AND LIFTING MEMBER

CROSS-REFERENCE TO RELATED APPLICATION DATA

This application claims the benefit of and priority to Provisional U.S. Patent Application Ser. No. 63/188,038 filed May 13, 2021, titled PATIENT INCONTINENCE PAD WITH INTEGRATED SUPPORT AND LIFTING MEMBER, the disclosure of which is incorporated herein in its entirety.

BACKGROUND

The present disclosure relates an incontinence pad for bedded patients, and more particularly to an incontinence pad with an integrated support and lifting member for bedded patients.

In order to change incontinence pads for bedded or bedridden patients, the patient must be moved or rolled onto one side and held in that position while the patient is cleaned, and the pad rolled or folded in a sanitary manner. The pad is then partially replaced by urging a new pad under the patient's side, after which the patient is then moved or rolled back onto her back to remove the soiled pad and position the clean pad in place.

Often the entire process is performed by one individual, such as a nurse, orderly, volunteer or other healthcare personnel. And, the potential for back injury when handling such patients that are unable to assist or move of their own accord is high, especially with large and/or obese patients. These injuries often result in medical and workers' compensation costs.

In the healthcare industry, a major cause of injuries is unsafe lifting practices, particularly when handling bedded or bedridden patients. This is particularly so when patients are bedridden and unable to assist or move on their own, and must be turned frequently in order to prevent pressure ulcers. The simple task of turning bedridden patients can be a challenging, and moving bedridden patients can be even more difficult and may result in injury to healthcare personnel using unsafe lifting practices.

Accordingly, there is a need for an improved patient incontinence pad. Desirably, such an incontinence pad includes an integrated support and lifting member. More desirably still, such an incontinence pad absorbs excretions, such as urine, feces and other bodily fluids, and provides an integrated, separable support and lifting member that allows for readily supporting a patient on the patient's side while removing and replacing the pad.

More desirably still, the separable support and lifting member can be used with the incontinence pad and independently of the pad, and the patient can be moved or rolled without the healthcare personnel directly or physically handling the patient. And, still more desirably, the entire integrated pad and support and lifting member can be readily disposed of with other medical wastes, without special handling procedures.

SUMMARY

According to one aspect an easily changed incontinence pad includes a main body having an upper portion and a lower portion and an incontinence member positioned on the lower portion. A support and lifting member forms the upper portion which is integrated with and separable from the lower portion. The main body is a generally T-shaped body, and the support and lifting member forms first and second arms of the T-shaped body.

The incontinence member can be an absorbent pad. In an embodiment, the incontinence pad is irremovably affixed to the main body.

The incontinence pad includes a weakened region between the upper portion and the lower portion. The weakened region can be, for example, a perforation line between the support and lifting member and the lower portion.

A fastening system can be positioned on an end of one or both of the first and second arms of the support and lifting member. In an embodiment, the fastening system is a hook and loop fastening system having hook portion and a loop portion. The hook portion and the loop portion can be positioned on a same surface of the support and lifting member.

In an embodiment, the main body is formed from a liquid impervious material. The liquid impervious material can be, for example, a composite material.

In another aspect a method of changing an incontinence pad for a patient in a bed, patient having proximal and distal sides, the bed having proximal and distal bedrails, is disclosed.

The method can include providing a first incontinence pad having a main body having an upper portion and a lower portion, an incontinence member positioned on the lower portion, and a support and lifting member forming the upper portion, the upper portion integrated with and separable from the lower portion, wherein the main body being a generally T-shaped body, the support and lifting member forming proximal and distal arms of the T-shaped body.

In methods, a patient is rolled onto the patient's distal side, and the proximal arm of the T-shaped body is secured to the distal bedrail. The lower portion of the first incontinence pad can then be separated from the proximal arm of the T-shaped body. The lower portion of the first pad can then be gathered as by rolling or folding toward the patient. A second incontinence pad is then positioned under the first incontinence pad and the proximal arm of the T-shaped body of the first pad is released from the distal bedrail.

In a method the support and lifting member includes a fastening system at an end of the arms and the step of securing the proximal arm of the T-shaped body to the distal bedrail, includes securing an end of the proximal arm to the bedrail by the fastening system. One such system can be a hook and loop fastening system having a hook portion and a loop portion. The hook portion and the loop portion can be positioned on a same surface of the proximal arm.

These and other features and advantages of the present invention will be apparent from the following detailed description, in conjunction with the appended claims.

DETAILED DESCRIPTION

While the present device is susceptible of embodiment in various forms, there is shown in the figures and will hereinafter be described a presently preferred embodiment with the understanding that the present disclosure is to be considered an exemplification of the device and is not intended to be limited to the specific embodiment illustrated.

Figure 1:
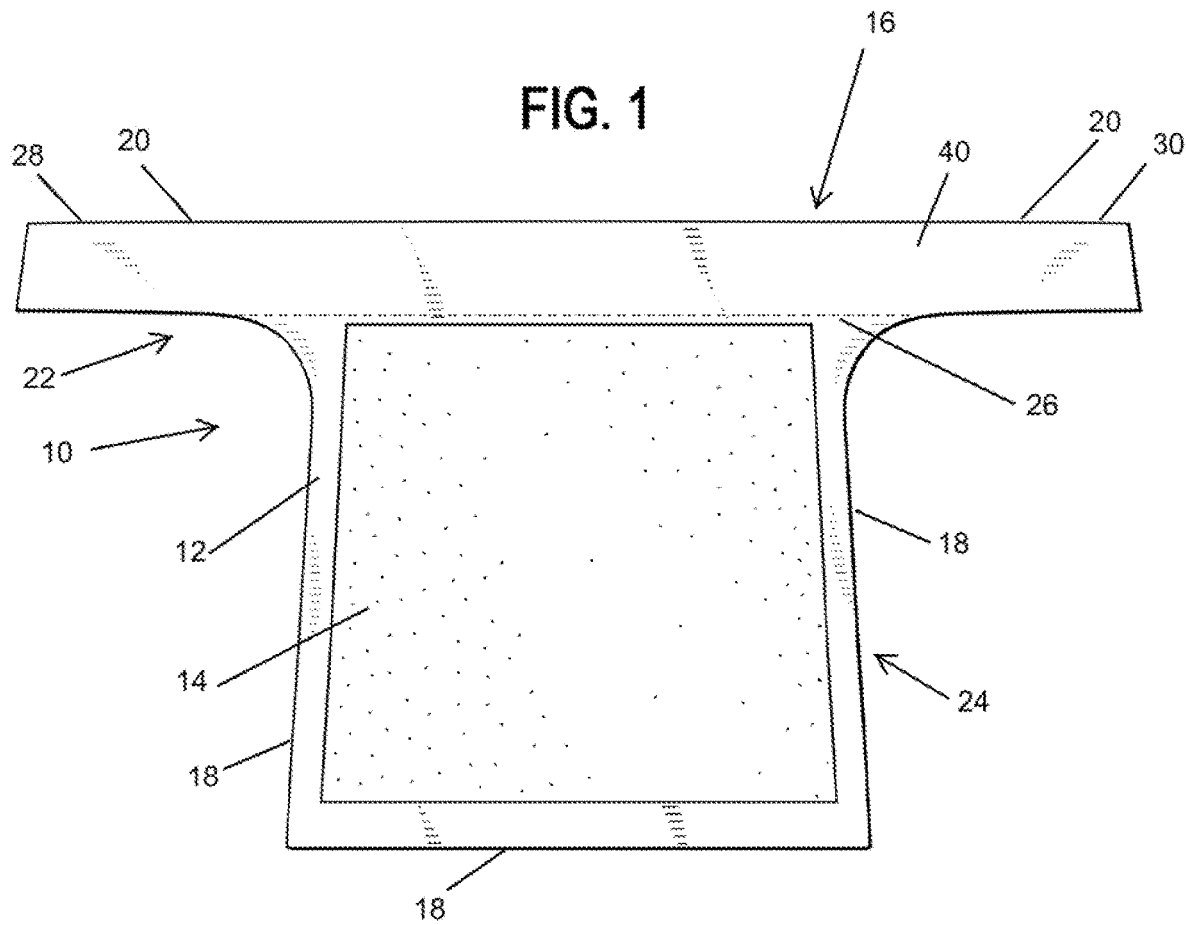
FIG. 1 is a top view of an embodiment of an incontinence pad with an integrated support and lifting member.

FIG. 1 illustrates an example of an incontinence pad with integrated support and lifting member 10. The pad 10 includes a main body 12, an incontinence member 14, such as an absorbent member or absorbent pad, and a support and lifting member 16. The support and lifting member 16 is integrated with, but separable from the main body 12. In embodiments, the absorbent pad 14 is integral with the main body 12. That is, the absorbent pad 14 may not be removable from the main body 12. In embodiments, the absorbent pad 14 extends toward by not to the edges 18 of the main body 12. Alternatively, although not shown, the absorbent pad can extend to the edges of the main body.

The pad 10, in its entirety, has a general T-shape. The support and lifting member 16 is at the top portion 22 of the main body 12 as arms 20 of the T. A lower portion 24 of the main body 12 has the absorbent pad 14 is affixed thereto. A separating element 26 is formed between the support and lifting member 16 and the main body lower portion 24. In embodiments, the separating element 26 is a weakened area in the material that forms the main body 12 and support and lifting member 16, such as a perforation, a thinned region, or the like, that facilitates ready separation of the support and lifting member 16 from the main body lower portion 24.

The pad 10 is used in an environment in which it may be subjected to bodily excretions and fluids, such as urine, feces, blood and the like. As such, in embodiments the absorbent pad 14 can be formed from an absorbent material, such as organic, inorganic or a combination of organic and inorganic materials, wovens, non-wovens, composites and the like, that may include (may have integrated therein) a superabsorbent material. Such materials will be recognized by those skilled in the art. The pad 10, in its entirety, is sized to approximately cover a substantial portion of a bed B on which a patient P is positioned, that may otherwise become soiled.

Further, because of the environment in which the pad 10 is used the main body 12 and integrated support and lifting member 16 are preferably formed from a relatively high-strength liquid impervious material. The material may be a composite material, such as a high-strength non-woven material laminated or otherwise adhered to a liquid impervious sheet, such as a polymeric material sheet.

The ends 28, 30 of the support and lifting member 16, i.e., the ends of the arms 20, include a fastening system 32. In an embodiment the fastening system 32 is securing elements, such as a hook and loop fastening system, for example, VELCRO® or like fasteners. The parts of the system, that is the hook portion 34 and the loop portion 36 can be provided on the same side or surface 38 of the arm 20 or on opposite surfaces or side 38, 40 of the arm 20. In a present embodiment the hook portion 34 and the loop portion 36 are on the same surface or side 38 of the arm 20, as is discussed in more detail below. The fastening systems 32 are provided on both "arms" or ends 28, 30 of the support and lifting member 16.

Figure 2:
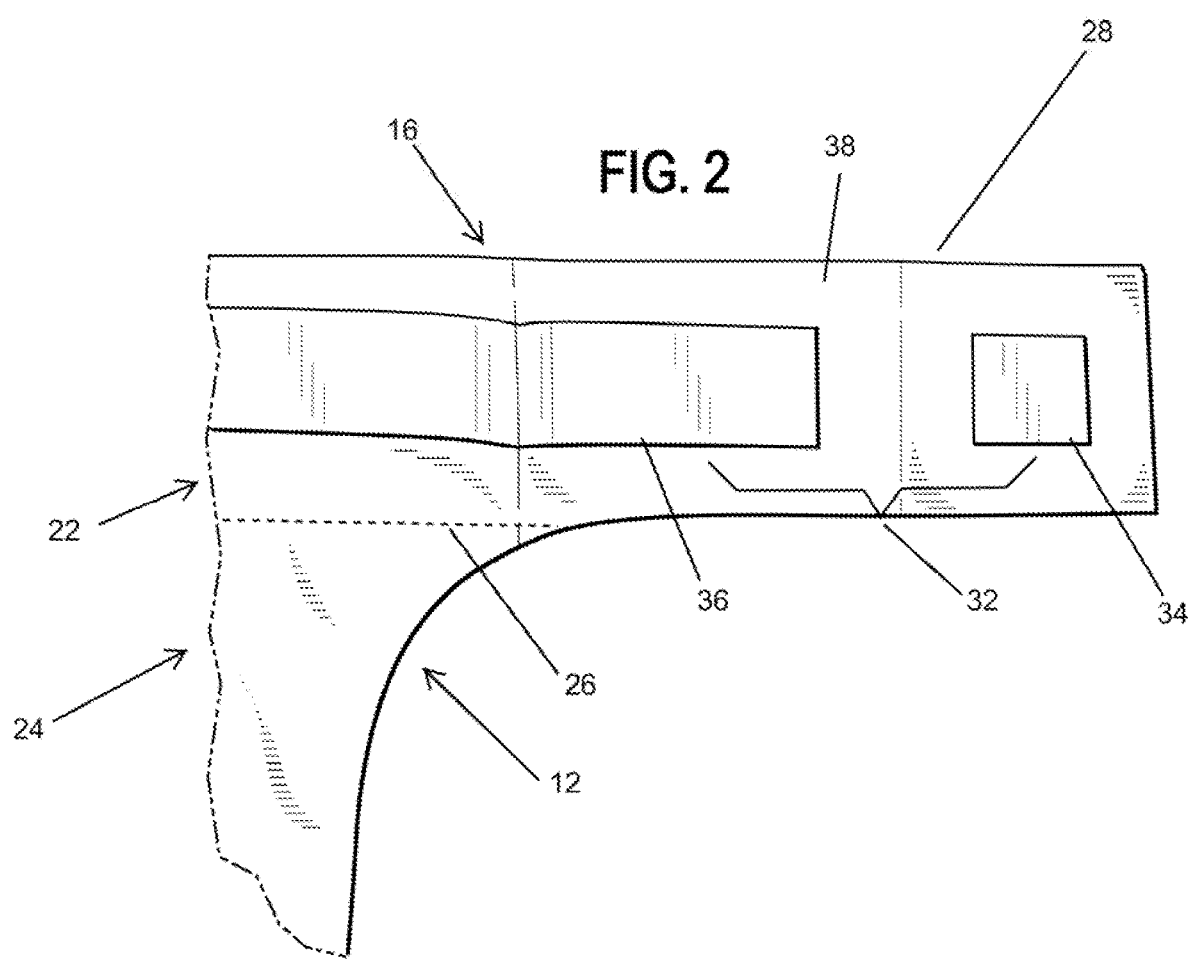
FIG. 2 is an enlarged partial rear view of the incontinence pad, showing an end of the support and lifting member in an unfolded state.
Figure 3:
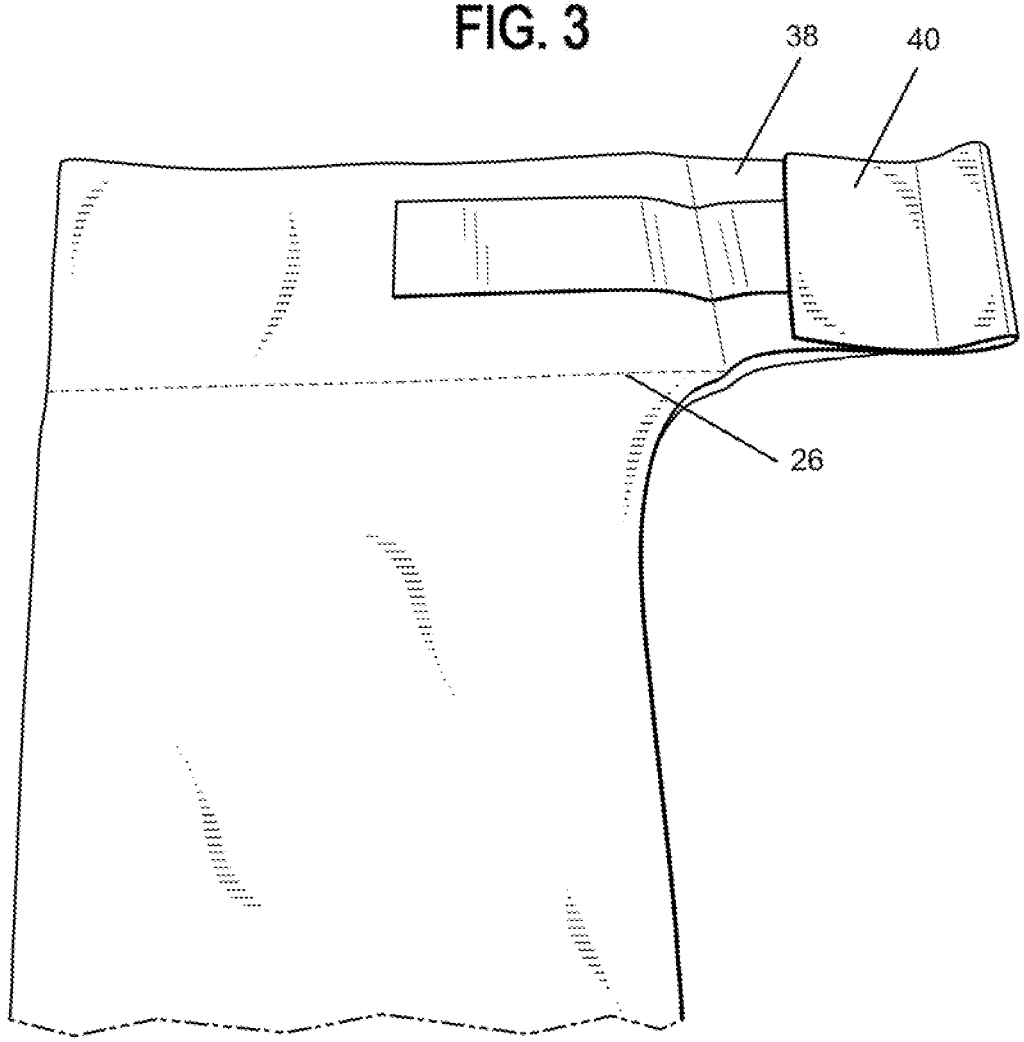
FIG. 3 is a view similar to FIG. 2 showing the end of the support and lifting member in a folded state.

As seen in FIG. 2, one portion of the fastening system, such as the hook portion 34 is provided as a smaller discrete element, such as a patch of material, whereas the other portion of the system, such as the loop portion 36, is provided as an elongated strip of material. This permits adjusting the length of and tension on the support and lifting member 16, and the position of the patient P.

Figure 4:
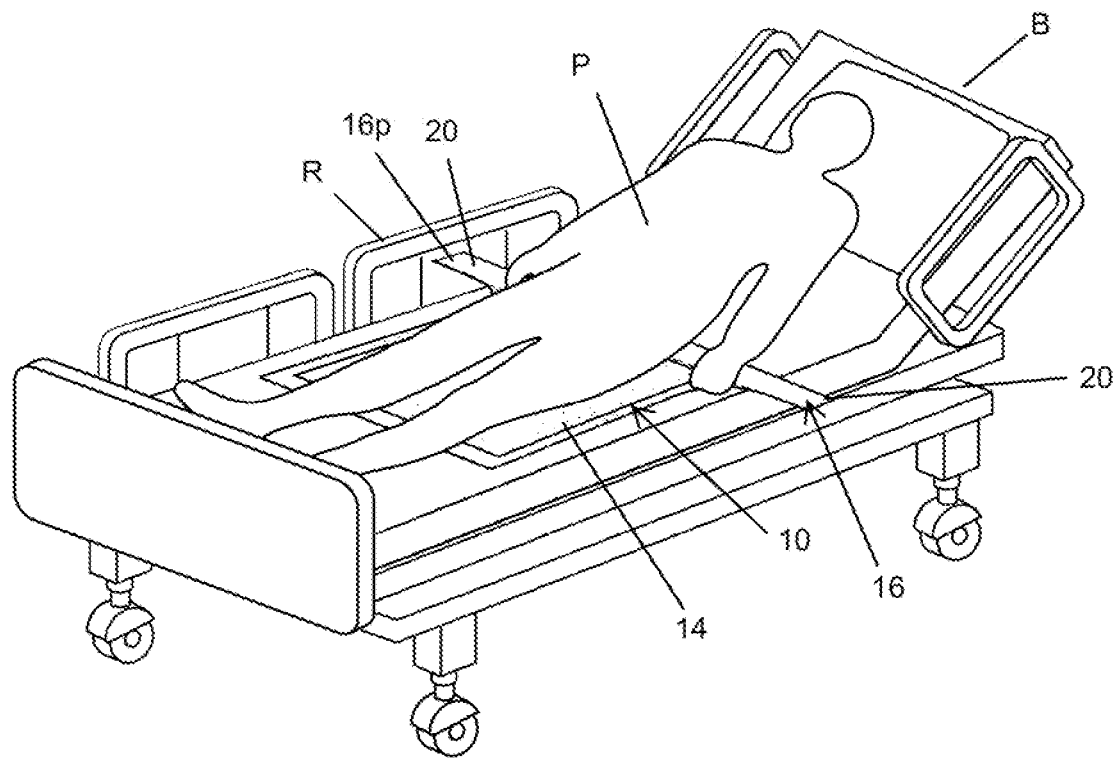
FIG. 4 illustrates the incontinence pad in an in-use state with a patient positioned on the pad on her back.
Figure 5:
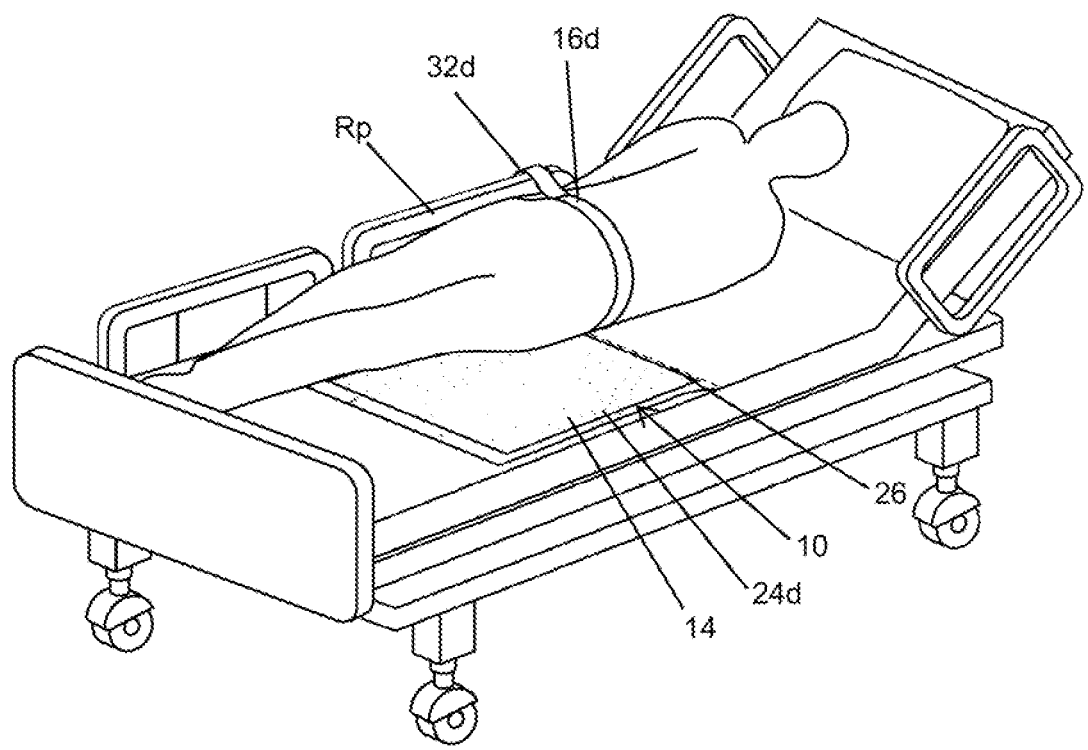
FIG. 5 illustrates the incontinence pad in an in-use state with a patient positioned on the pad rolled onto her side.

Referring now to FIGS. 4 and 5, in one contemplated use, a pad 10 is positioned on a bed B and a patient P is positioned on the pad 10. The arms 20 extend outwardly from the patient P toward the sides of the bed B. Typically, the patient P is in a hospital or like bed that has bed rails R on the sides of the bed to prevent the patient P from falling out of the bed B. For purposes of the in-use description of the pad 10, reference will be made to a proximal end of the support and lifting member 16p (and arm) and proximal bed rail Rp, and to a distal end of the support and lifting member 16d (and arm) and distal bed rail (not shown).

To replace the pad 10 (a "first" pad), which can be performed by one individual without physical contact with the patient P, referring to FIG. 5, the patient P is rolled onto a side facing the proximal bed rail Rp. The distal end of the support and lifting member 16d is drawn up over and across the patient's body toward the proximal bed rail Rp. As the distal end of the support and lifting member 16d is drawn to the proximal bed rail Rp, the distal end of the member 16d is pulled around the proximal bed rail Rp and the distal end fastening system 32d is used to secure the distal end of the member 16d to the proximal bed rail Rp (the opposite bed rail) with the patient P positioned on her side to secure the patient P in this position.

Briefly, as noted above, the first and second portions of the fastening system 32 (e.g., the hook and loop portions 34, 36) can be positioned on the same surface 38 of the arms 20. This permits readily looping the arm 20 around the bed rail Rp and fastening the hook and loop portion 34, 36 to each other. In addition, where one portion may be a patch and the other an elongated strip, this permits adjusting the amount of movement or roll (e.g., the position) of the patient and/or the tension on the support and lifting member 16.

With the patient P on her side, the distal portion 24d of the main body lower portion 24 is then separated from the support and lifting member 16 and the lower portion 24 is positioned on the bed B. The patient P can then be wiped clean and the cleaning materials can be placed on the lower portion 24. The lower portion 24 can then be folded or rolled into itself to contain any excretions or bodily fluids, and to contain any cleaning materials, such as cleaning wipes or the like.

A new (second) pad can then be wedged under the patient's (distal) side and under the first (or rolled soiled) pad 10. The distal end fastening system 32d of the first pad support and lifting member 16 can then be released to allow the patient P to roll back onto her back, the first pad 10 removed, and the second pad can then be adjusted beneath the patient. If needed, the patient P can be lifted using the first pad support and lifting member 16 to further adjust the new (second) pad. The patient P can then be lowered back onto the new (second) pad and the first pad support and lifting member 16 removed from beneath the patient P.

It will be appreciated that the in-use description or method of changing an incontinence pad 10 can take many variations and that all such variations using the present incontinence pad with integrated support and lifting member 10 are within the scope and spirit of the present disclosure.

It will also be recognized and appreciated that the present incontinence pad with integrated support and lifting member 10 can be used to lift the patient P for purposes other than changing a pad. For example, if a patient P is to be moved or rolled from one side to another, the support and lifting member 16 can be used (with or without securing it to a bed rail) to, for example move a patient to avoid bedsores, for examining various locations of the patient's body and the like.

It will be appreciated that the present incontinence pad with an integrated support and lifting member 10 provides significant advantages over known incontinence pads. First, by virtue of the integrated support and lifting member 16, the patient P can be moved or rolled without the healthcare personnel directly or physically handling the patient P. And, the patient P can be moved or rolled by one individual, in most cases, without assistance.

It will be further recognized that the present pad 10 includes an absorbent pad or member 14 to absorb excretions, such as urine, feces and other bodily fluids, and provides an integrated, separable support and lifting member 16 that allows for readily supporting a patient P on the patient's side while removing and replacing the pad 10.

Moreover, the separable support and lifting member 16 can be used independently of the incontinence pad 14 to facilitate moving or rolling the patient P to, for example, avoid the bedsores and other maladies that can affect bed-ridden patients. Further still, the present incontinence pad with integrated support and lifting member 10 can be fabricated from materials that permit disposal as conventional medical waste, thus requiring no special handling procedures beyond those needed for other medical wastes.

Features from any one of the embodiments described above may be implemented in, combined or used together with, or replace features from any of the other embodiments described above. That is, the various features from any of the embodiments above are usable together with the other embodiments described herein.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular. In addition, it is understood that terminology referring to orientation of various components, such as "upper" or "lower" is used for the purposes of example only, and does not limit the subject matter of the present disclosure to a particular orientation.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover all such modifications as fall within the scope of the claims.

What is claimed is:

1. A disposable incontinence pad, comprising:
a main body having integral upper and lower portions, the upper and lower portions separated by a single weakened line of separation;
an absorbent incontinence member positioned wholly on the lower portion, the absorbent incontinence member being irremovably affixed to the main body; and
a single support and lifting member forming the entirety of the upper portion, the upper portion integrated with and separable from the lower portion along the single weakened line of separation,
wherein the main body is a generally T-shaped body, the separable support and lifting member forming first and second arms of the T-shaped body.

2. The incontinence pad of claim 1, wherein the absorbent incontinence member is an absorbent pad.

3. The incontinence pad of claim 1, wherein the single weakened line of separation is a perforation line between the support and lifting member and the lower portion.

4. The incontinence pad of claim 1, further including a fastening system on an end of one or both of the first and second arms of the support and lifting member.

5. The incontinence pad of claim 4 wherein the fastening system is a hook and loop fastening system having hook portion and a loop portion.

6. The incontinence pad of claim 5 wherein the hook portion and the loop portion are positioned on a same surface of the support and lifting member.

7. The incontinence pad of claim 1 wherein the main body is formed from a liquid impervious material.

8. The incontinence pad of claim 7, wherein the liquid impervious material is a composite material.

9. A method of changing a disposable incontinence pad for a patient in a bed, patient having proximal and distal sides, the bed having proximal and distal bedrails, the method comprising:
providing a first disposable incontinence pad having a main body having integral upper and lower portions, the upper and lower portions separated by a single weakened line of separation, an absorbent incontinence member positioned wholly on the lower portion and irremovably affixed to the lower portion, and a single support and lifting member forming the upper portion, the upper portion integrated with and separable from the lower portion along the single weakened line of separation, wherein the main body is a generally T-shaped body, the separable support and lifting member forming proximal and distal arms of the T-shaped body and forming the entirety of the upper portion;
rolling a patient onto the patient's distal side;
securing the proximal arm of the T-shaped body to the distal bedrail;
separating the lower portion of the first incontinence pad from the proximal arm of the T-shaped body;
rolling or folding the lower portion of the first incontinence pad toward the patient;
positioning a second disposable incontinence pad under the first incontinence pad; and
releasing the proximal arm of the T-shaped body from the distal bedrail.

10. The method of claim 9, wherein the support and lifting member includes a fastening system at an end of the arms and wherein the step of securing the proximal arm of the T-shaped body to the distal bedrail, includes securing an end of the proximal arm to the bedrail by the fastening system.

11. The method of claim 10, wherein the fastening system is a hook and loop fastening system having a hook portion and a loop portion.

12. The method of claim 11, wherein the hook portion and the loop portion are positioned on a same surface of the proximal arm.

13. The method of claim 10, wherein the proximal arm of the T-shaped body is secured around the distal bedrail.

* * * * *